(12) United States Patent
Hill et al.

(10) Patent No.: US 6,511,592 B1
(45) Date of Patent: Jan. 28, 2003

(54) BIOSENSOR FOR PENTACHLOROPHENOL

(75) Inventors: Hugh Allen Oliver Hill, Oxford (GB); Luet-Lok Wong, Oxford (GB); Weihong Xie, Oxford (GB); Jonathan Peter Jones, Bolton (GB)

(73) Assignee: ISIS Innovation Limited (GB)

( * ) Notice: Subject to any disclaimer, the term of this patent is extended or adjusted under 35 U.S.C. 154(b) by 0 days.

(21) Appl. No.: 09/600,749

(22) PCT Filed: Feb. 5, 1999

(86) PCT No.: PCT/GB99/00391

§ 371 (c)(1),
(2), (4) Date: Oct. 2, 2000

(87) PCT Pub. No.: WO99/40218

PCT Pub. Date: Aug. 12, 1999

(30) Foreign Application Priority Data

Feb. 5, 1998 (GB) .............................................. 9802503

(51) Int. Cl.⁷ ........................................... G01N 27/327
(52) U.S. Cl. ................. 205/777.5; 204/403.1; 204/403.14
(58) Field of Search ................ 204/403, 403.1, 204/403.14; 205/777.5

(56) References Cited

U.S. PATENT DOCUMENTS

| | | | |
|---|---|---|---|
| 4,808,517 A | | 2/1989 | George et al. .................. 435/8 |
| 5,512,478 A | * | 4/1996 | Orser et al. ............. 435/252.33 |
| 5,792,622 A | | 8/1998 | Botsford ....................... 435/29 |
| 6,083,367 A | * | 7/2000 | Suzuki ........................ 204/415 |

OTHER PUBLICATIONS

Abstract of Xun et al. ("Confirmation of oxidative dehalogenation of pentachlorophenol by a Flavobacterium pentachlorophenol hydroxylase", J. Bacteriol. Sep. 1992, 5745–5747, vol. 174, No. 17).*
Kjellen et al. ("Enzyme Electrode for Phenol", Biotechnol. Bioeng. (1980), 22(2), 299–310).*
K. B. Male et al., "Optimization and Characterization of a Flow Injection Electrochemical System for Pentachlorophenol Assay," *Anal Chem.*, vol. 70, pp. 4134–4139 (Oct. 1998).
C. Saby et al., "A Combined Chemical and Electrochemical Approach Using Bis(trifluoroacetoxy)iodobenzene and Glucose Oxidase for the Detection of Chlorinated Phenols," *Anal. Chem.*, vol. 69, pp. 4324–4330 (Nov. 1997).
C. Saby et al., "A Biosensor System for Chlorophenols Using Chloroperoxidase and a Glucose Oxidase Based Amperometric Electrode," *Electroanalysis*, vol. 10, pp. 7–11 (1998). Month Unknown.

* cited by examiner

Primary Examiner—T. Tung
Assistant Examiner—Alex Noguerola
(74) Attorney, Agent, or Firm—Lahive & Cockfield LLP; Anthony A. Laurentano; Peter C. Lauro

(57) ABSTRACT

A sensor for pentachlorophenol comprises a sensor electrode carrying a pentachlorophenol hydroxylase, and a counter electrode. An assay method comprises maintaining a potential difference between the electrodes and observing a current associated with enzyme-catalyzed oxidation of the pentachlorophenol.

8 Claims, 2 Drawing Sheets

BIOSENSOR FOR PENTACHLOROPHENOL

Pentachlorophenol (PCP) and other polyhalogenated phenols constitute a major group of environmental pollutants. These compounds are widely used as wood preservatives, fungicides, insecticides and bactericides. PCP is a biocide and used primarily for wood preservation. It is ubiquitous in the environment and considered a priority pollutant by the U.S. Environmental Protection Agency. The Dutch proposal for soil contamination limit is ca. 5 mg/kg dry weight. Management of pollution by PCP (or indeed by any man-made chemical) of the environment involves monitoring and where necessary, remediation. For priority pollutants such as PCP, it is therefore highly desirable to have an easy, point-of-use, real-time sensor—the development of such a sensor is the subject of this application.

BACKGROUND

The monooxygenase enzyme pentachlorophenol hydroxylase (PCPH) is responsible for the first oxidation step in the pentachlorophenol degradation pathway in Flavobacterium sp. (ATCC 39723). PCPH catalyses the oxidation of pentachlorophenol (PCP) to 2,3,5,6-tetrachloro-p-hydroquinone (TeCH), a reaction which requires two equivalents of NADPH and one molecule of dioxygen (Scheme 1). The gene encoding this 65 kDa flavoenzyme has been cloned and sequenced, and the enzyme has been over-expressed in E. coli.

The substrate range of PCPH has been investigated. It was found that the enzyme has an absolute requirement for the phenol group and also a substituent at the ortho position to the phenol. Thus, benzene and halobenzenes are not substrates, nor does PCPH attack 3,5-dichlorophenol although 2,3-dichlorophenol is a poor substrate.

Scheme 1
The oxidation of pentachlorophenol by PCPH

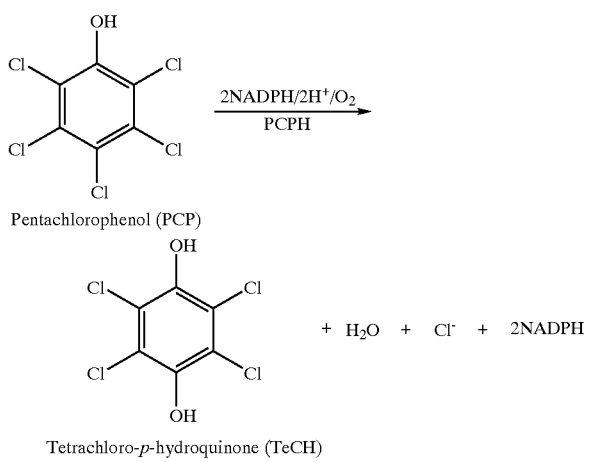

Pentachlorophenol (PCP)

Tetrachloro-p-hydroquinone (TeCH)

THE INVENTION

Figure 1:
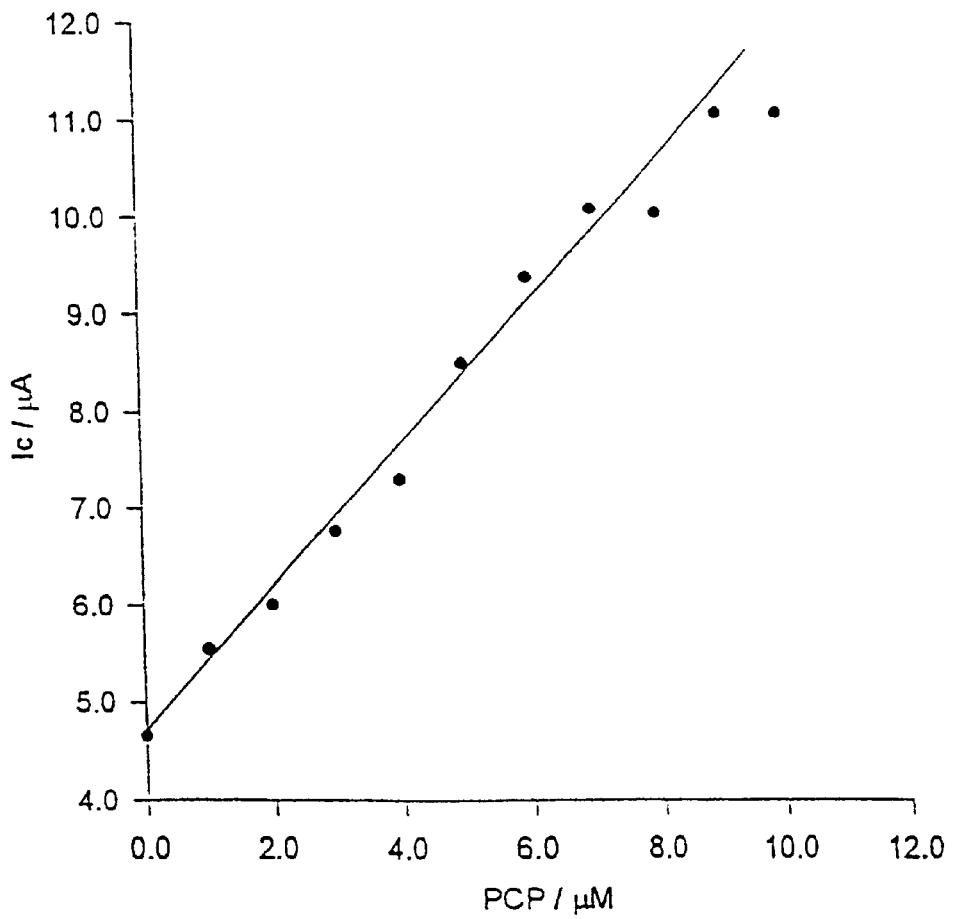
FIG. 1 depicts the concentration dependence of the catalytic current at a PCPH concentration of 87 $\mu$M.

This invention results from the discovery that PCP can be oxidised enzymatically, with an electrode replacing NADPH, the normal source of electrons required for catalysis.

In one aspect the invention provides a sensor, comprising a sensor electrode composed of an electrically conducting material and comprising at an external surface thereof a pentachlorophenol hydroxylase or a mutant version thereof, and a counter electrode, means for maintaining the sensor electrode at a predetermined potential, and means for observing a current passing between the sensor electrode and the counter electrode.

In another aspect the invention provides a method of assaying for pentachlorophenol or other aromatic compound in a fluid sample, which method comprises providing a sensor electrode composed of an electrically conducting material and comprising at an external surface thereof a pentachlorophenol hydroxylase or a mutant version thereof, and a counter electrode, in contact with the fluid sample, maintaining the sensor electrode at a predetermined potential, and observing a current passing between the sensor electrode and the counter electrode associated with enzyme-catalysed oxidation of pentachlorophenol (or other halogenated or non-halogenated aromatic compound) in the sample.

The enzyme used in the experimental section below is PCPH itself. As noted, PCPH has an absolute requirement for an aromatic hydroxyl group, and also for a halogen or other substituent ortho to the hydroxyl group. It will be possible to modify the PCPH enzyme, e.g. by site-directed mutagenesis, to provide a mutant enzyme. Such mutant enzymes may have altered e.g. broadened substrate specificity or altered e.g. improved catalytic efficiency. In particular, the use is envisaged of mutant enzymes which can oxidise halogenated aromatic compounds to halogenated phenols. The use of wild-type PCPH enzyme together with one more mutant enzymes is also envisaged.

The electrically conductive material of the working electrode can be gold or, preferably carbon. The latter is usually partially oxidised so that the enzyme can be immobilised on the surface. The auxiliary or counter electrode is usually a silver electrode which is pretreated in a solution containing chloride ions so that it acts as a quasi-reference electrode.

Preferably the sensor or working electrode consists of an array of microelectrodes. A microelectrode has a very small charging capacitance, shows radial diffusion kinetics, has a rapid response time and simply and easily interpreted current-voltage behaviour. Furthermore only two electrodes are required, viz the working electrode and a counter electrode. Although the magnitude of the current from an individual microelectrode is low, this can be offset, with an improved signal to noise ratio, if an array of hundreds or thousands of microelectrodes is used. In a suitable array, each microelectrode has a diameter preferably in the range of 0.1–1.0 $\mu$m, and is spaced from its neighbours by a distance of preferably 1–100 $\mu$m.

The enzyme may be applied to a surface of the electrode simply by dipping the electrode in a solution of the enzyme and allowing the volatile liquid to evaporate. Or the enzyme can be immobilised on the electrode surface e.g. by derivatising the surface with the carbo-diimide material DDC (1-cyclohexyl-3-(2-morpholinoethyl)carbodiimide metho-p-toluene sulphonate). Or the enzyme may be immobilised in a self-supporting layer of gelatine or other hydrophilic polymer on the electrode surface. The amount of enzyme on the surface of the electrode is one of the factors which determines the size of the electric current that results from catalytic oxidation of PCP or other analyte. The amount of enzyme applied to the electrode can be adjusted to correlate with expected analyte concentrations in fluid samples.

In the experimental section below, bare edge-plane graphite (EPG) electrodes have been used. However, it is possible to pretreat an electrode with a material which screens the bare electrode surface from the enzyme but which also presents correct functional groups to interact with the enzyme to allow the direct electrochemistry to be observed. Such surface modification is expected to reduce any absorption of the enzyme on the electrode and improve the quality and the stability of the electrochemical response obtained. An example of a surface modifier that is expected to be useful in this context is poly-L-lysine.

Preferably the enzyme on the surface of the electrode is surrounded by a protective membrane. This may be a dialysis membrane. Alternatively the membrane may be a layer of cellulose acetate or other hydrophilic polymer, e.g. as formed by dipping the coated electrode into a solution of the hydrophilic polymer. A function of the protective membrane is to prevent blocking of reactive enzyme sites by insoluble components (including PCP which has low solubility in water) of the fluid sample being tested. If the sample contains PCP dissolved in an organic solvent, then a protective membrane can prevent bulk organic solvent from contacting and denaturing enzyme on the sensor electrode surface, while allowing passage of dissolved PCP.

It is an advantage of the invention that a mediator is not required, and that enzyme catalysed oxidation of the substrate can be detected directly.

A sensor according to the invention has, in addition to a sensor electrode, a counter electrode; means for maintaining the sensor electrode at a predetermined potential; and means for observing a current passing between the sensor electrode and the counter electrode. These additional components can be of a kind routinely used in biosensors. In the experimental work below, the sensor electrode was maintained at a potential of 400 mV, but this value could be varied within a range of $-800$ to $+50$ MV. The overall design, size and shape of the sensor may be conventional.

The fluid sample to be analysed may be aqueous or non-aqueous, polar or non-polar organic solvent in which the enzyme substrate, typically PCP, is sufficiently soluble. Where PCP contamination of particulate material such as soil is being determined, a fluid extract may need to be made. Where PCP contamination of water is being determined, the sample may need to be concentrated, as described in the experimental section below. The techniques described herein are in principle suitable for detecting PCP at concentrations in the range 1 nM to 1 M, preferably 1 to 100 $\mu$M.

Experimental
Recombinant PCPH Expression and Purification

The gene encoding PCPH was amplified by the polymerase chain reaction (PCR) from the total cellular DNA isolated from a culture of Flavobacterum sp. (ATCC 53874) using oligonucleotide primers designed on the basis of the published nucleotide sequence. The primers were designed to incorporate appropriate restriction sites for cloning into a number expression vectors. One of the expression vectors utilises a tac promoter, and the recombinant vector containing the PCPH gene expresses the PCPH enzyme to high level in E. coli strain $DH_{5\alpha}$. The recombinant protein was isolated and purified to homogeneity by two anion exchange chromatography steps. The purified protein had identical spectroscopic properties and PCP oxidation activities as those reported in the literature.

Direct Electrochemistry Studies

Most previous publications on the electrochemistry of flavin-containing proteins and enzymes focused on flavoproteins or the indirect, mediated electrochemistry of flavoenzymes; only a few papers have appeared which described the direct electrochemistry of flavoenzymes such as glucose oxidase, fumarate reductase, and xanthine oxidase, although in these cases it was difficult to discern whether or not the electrochemistry of the free flavin was interfering.

The direct electrochemistry of PCPH was investigated using direct-current cyclic voltammetry, in a glove box under an atmosphere of dinitrogen ($O_2$<4 ppm). The cyclic voltammogram (CV) of PCPH on a bare edge-plane graphite (EPG) electrode showed a pair of redox waves with a redox potential, taken as the mean of the anodic and cathodic peak potentials, of $-512$ mV vs. SCE. The cathodic peak currents were proportional to the square root of the scan rate from 2 $mVs^{-1}$ to 200 $mVs^{-1}$, indicating a diffusion-controlled process. The peak-to-peak separation was about 30 mV and increased with the scan rate, consistent with quasi-reversible two-electron electron transfer. The addition of substrate did not affect the electrochemical response.

Flavoproteins are notorious for easily losing the co-enzyme FAD. Preliminary experiments were therefore undertaken which indicated that the electrochemical response from PCPH was indeed due to the FAD co-enzyme within the active site of the intact enzyme and not to free FAD which had disassociated from the enzyme during the experiments.

Electrochemically Driven PCP Oxidation

The direct electrochemistry of PCPH, at $-800$ mV, was carried out in the presence of the PCP substrate and in an aerobic environment in order to assess whether it was possible to drive the PCP oxidation reaction electrochemically. After 30 mins, a new pair of redox waves were observed at 60 mV, which is consistent with the redox potential of the product, TeCH, by comparison with the CV of an authentic sample. Analysis of the organic extract of the solution by gas chromatography also showed the presence of TeCH, the product of PCP oxidation. Furthermore, no product was detected, either electrochemically or by gas chromatography, with free FAD under the same conditions. This showed that PCP oxidation was effected enzymatically, with the electrode replacing NADPH, the normal source of electrons required for catalysis.

PCP Concentration-dependent Catalytic Currents: Biosensor Development

The dependence on PCP concentration of the catalytic current arising from electrochemically driven oxidation of PCP by PCPH was investigated with the view of developing an amperometric biosensor. The catalytic current was determined for different PCP and enzyme concentrations as well as different electrode preparations.

Figure 2:
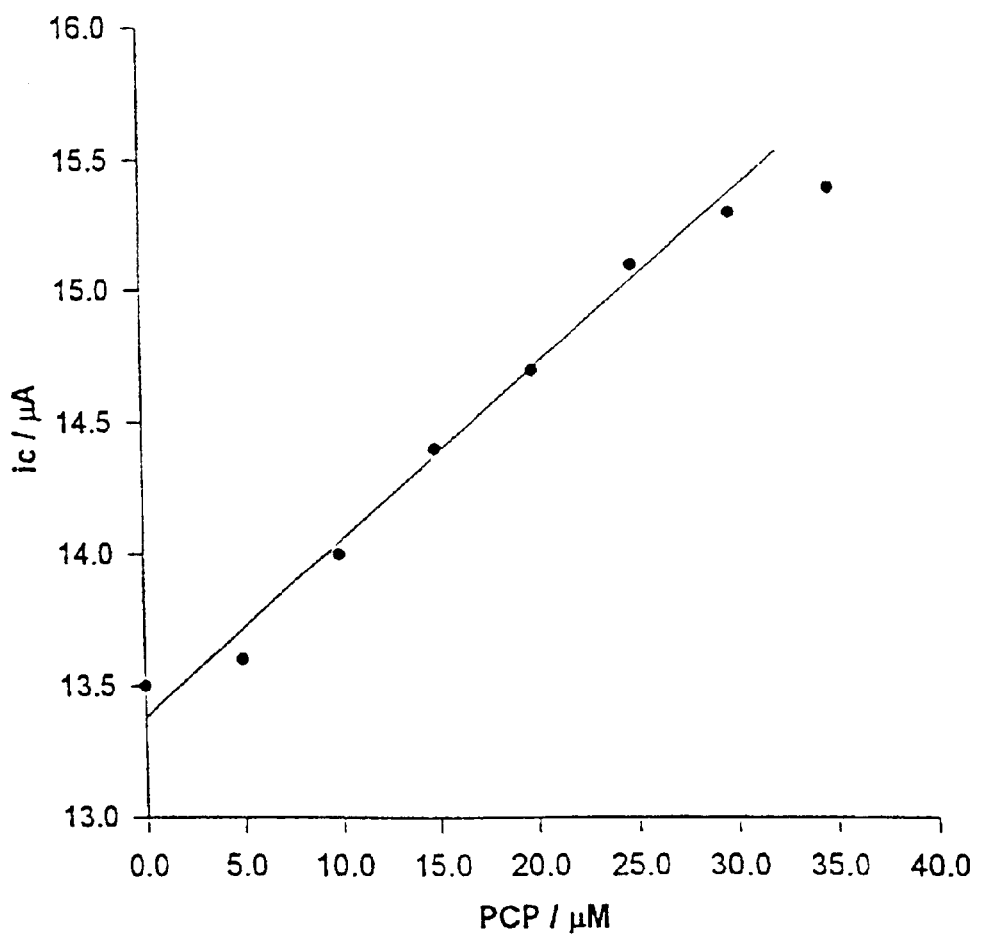
FIG. 2 depicts the concentration dependence of the catalytic current at a PCPH concentration of 196 $\mu$M.

PCPH enzyme was immobilised by natural evaporation of a drop of a buffered solution of the enzyme on an EPG electrode. The coated electrode was wrapped with a dialysis membrane (molecular weight cut-off 3500) which was secured by means of either standard laboratory polyethylene film or an O-ring. The electrode, with the immobilised enzyme thus protected by the membrane, was dipped into a solution of PCP in 99.7% ethanol. The concentration dependence of the catalytic current became linear within certain limits. For example, with a PCPH concentration of 87 $\mu$M in the solution which was evaporated from the electrode surface, the linear range extended to ca. 8 $\mu$M (FIG. 1). With a higher enzyme concentration of 196 $\mu$M, the linear range extended to ca. 25 $\mu$M (FIG. 2). The absolute values of the catalytic currents for each enzyme concentration varied between preparations but the gradient of the plots of current vs. PCP concentration were identical, within experimental error.

Substrate Range Investigations

Samples from the environment contain many other compounds which may be substrates for PCPH and therefore interfere with PCP biosensing. The substrate range of the PCPH enzyme was therefore investigated. The compounds tested as possible substrates were toluene, biphenyl, phenylcyclohexane, 1-phenylcyclohexene, diphenylmethane, bibenzyl and hexadecane, included as a model long-chain alkane. None of the compounds except bibenzyl was oxidised by PCPH, as determined by gas chromatography. In the case of bibenzyl, a very small amount of product was detected by gas chromatography but this product was not chemically characterised.

A Biosensing Protocol for PCP

Based on the work described herein, the following protocols for PCP biosensing can be proposed.

Soil Samples

A 20 g sample of potentially contaminated soil is sonicated with 20 ml of acetone to extract the organics. The mixture is then centrifuged or simply filtered to remove particulates. Depending on the results of field trials, this centrifugation/filtration step may not even be necessary. The membrane-protected, PCPH-based PCP sensor can be dipped into the acetone solution and the PCP concentration measured directly. A soil contamination level of 5 mg PCP per kg dry weight and all of which is extracted into 20 ml of solvent corresponds to a final PCP concentration in the acetone of about 19 $\mu$M, which is comfortably within the detection limit of the PCP biosensor. These figures are a guide only because the extraction may not be 100% efficient and the volume of solvent recovered will not be exactly 20 ml.

Water Samples

The legal limit of PCP concentration in water is likely to be <10 $\mu gl^{-1}$; for the purpose of this calculation it will be assumed that the target concentration is 5 $\mu gl^{-1}$. This concentration (about 19 nM) is too low for direct measurement by the PCP biosensor, used in this experiment, though the use of an array of microelectrodes and other improvements are expected to extend the range of measurable concentrations. The proposed protocol therefore calls for extraction of PCP from a certain volume of potentially contaminated water by means of, for example, a Bond-Elut column (Varian), and then eluting the PCP off the column with a small volume of an organic solvent such as acetone or chloroform. Assuming that the elution will use 1 ml of organic solvent, then since the PCP is biosensor can readily detect a concentration of 4 $\mu$M, the concentration factor is 4 $\mu$M/19 nM or 210, i.e., if 200 ml of water sample is extracted by means of a Bond-Elut column and the column eluted with 1 ml of an organic solvent, the target legal limit is readily detected. If larger volumes, such as 1 litre, were extracted, then repeat measurements with different electrodes can be made on the same sample.

Engineering of PCPH for Bioremediation Applications

Orser and co-workers have shown that PCPH has an absolute requirement for the phenol functionality. Thus pentachlorophenol but not pentachlorobenzene is oxidised by PCPH. This functional group specificity presumably arises from specific interactions between the phenol group and enzyme active-site side-chains. The most likely interaction is that of hydrogen bonding, e.g., one or more aspartate and/or glutamate side-chains within the PCPH active-site may form hydrogen bonds to the phenol, and the presence of such ionised side-chains will strongly disfavour the binding of hydrophobic compounds such as pentachlorobenzene.

The inventors have found conditions under which PCPH can be crystallised and the preparations of high diffraction quality crystals is in progress. They will determine the crystal structure of PCPH, with and without bound PCP, and identify the side-chains responsible for the specificity for phenol derivatives. These side-chains will then be changed by site-directed mutagenesis to hydrophobic ones. These mutants may then bind hydrophobic polyhalogenated aromatics and oxidise them to the phenol derivatives. For example, the mutants may oxidise penta- and hexachlorobenzene to PCP. The success of this approach will open up the exciting prospect of developing biosensors for the polychlorinated aromatics such as pentachlorobenzene which the wild-type PCPH will not bind.

What is claimed is:

1. A sensor, comprising: a sensor electrode composed of an electrically conducting material and comprising, at an external surface thereof, a pentachlorophenol hydroxylase or a mutant version thereof; a counter electrode; means for maintaining the sensor electrode at a predetermined potential; and means for observing catalytic current passing between the sensor electrode and the counter electrode arising from catalytic activity of the pentachlorophenol hydroxylase or the mutant version thereof.

2. A sensor as claimed in claim 1, wherein the pentachlorophenol hydroxylase or a mutant version thereof is surrounded by a permeable membrane.

3. A sensor as claimed in claim 1, wherein the sensor electrode comprises an array of microelectrodes.

4. A method of assaying for an aromatic compound in a fluid sample, which method comprises: providing a sensor electrode composed of a electrically conducting material and comprising, at an external surface thereof, a pentachlorophenol hydroxylase or a mutant version thereof, and a counter electrode; contacting the sensor electrode with the fluid sample; maintaining the sensor electrode at a predetermined potential; and observing catalytic current passing between the sensor electrode and the counter electrode associated with the electrochemical enzyme-catalyzed oxidation of the aromatic compound in the sample, by the pentachlorophenol hydroxylase or the mutant version thereof, to thereby assay for an aromatic compound in a fluid sample.

5. A method as claimed in claim 4, wherein the aromatic compound is a halogenated aromatic compound.

6. A method as claimed in claim 5, wherein the halogenated organic compound is pentachlorophenol.

7. A method as claimed in claim 4, wherein the pentachlorophenol hydroxylase or a mutant version thereof is surrounded by a permeable membrane.

8. A method as claimed in claim 4, wherein the fluid sample is in water or an organic solvent.

* * * * *